United States Patent
Maia et al.

(10) Patent No.: US 11,297,495 B2
(45) Date of Patent: Apr. 5, 2022

(54) MEDICAL IMAGE TRANSFER SYSTEM

(71) Applicant: BIOSENSE WEBSTER (ISRAEL) LTD., Yokneam (IL)

(72) Inventors: Daniel Maia, Madison, CT (US); Chris Aucone, Raritan, NJ (US); Jun Chen, Raritan, NJ (US); Yevgeniy Shkolnikov, Raritan, NJ (US)

(73) Assignee: Biosense Webster (Israel) Ltd., Yokneam (IL)

( * ) Notice: Subject to any disclaimer, the term of this patent is extended or adjusted under 35 U.S.C. 154(b) by 199 days.

(21) Appl. No.: 16/368,168

(22) Filed: Mar. 28, 2019

(65) Prior Publication Data
US 2019/0349755 A1    Nov. 14, 2019

Related U.S. Application Data

(60) Provisional application No. 62/668,473, filed on May 8, 2018.

(51) Int. Cl.
*H04W 12/00* (2021.01)
*H04W 12/06* (2021.01)
(Continued)

(52) U.S. Cl.
CPC ........... *H04W 12/033* (2021.01); *A61B 90/37* (2016.02); *G16H 70/20* (2018.01); *H04L 9/0891* (2013.01);
(Continued)

(58) Field of Classification Search
CPC .... H04W 12/033; H04W 12/06; A61B 90/37; A61B 34/20; A61B 2034/2074;
(Continued)

(56) References Cited

U.S. PATENT DOCUMENTS 7,720,521 B2    5/2010  Chang et al.
8,108,432 B2 *  1/2012  Westin .................. G16H 30/20
                                                707/792
(Continued)

FOREIGN PATENT DOCUMENTS

WO    WO 2009/137688 A2    11/2009
WO    WO 2014/130592 A1     8/2014

OTHER PUBLICATIONS

U.S. Appl. No. 62/668,473, entitled "Medical Image Transfer System," filed May 8, 2018.

(Continued)

*Primary Examiner* — Catherine Thiaw
(74) *Attorney, Agent, or Firm* — Frost Brown Todd LLC

(57) ABSTRACT

A transfer module, such as a single board computer having wireless communication capabilities, may be attached to an image guided surgery ("IGS") navigation system. Images, video, and data stored on the IGS navigation system may be moved to and stored on the transfer module in an encrypted format. The transfer module may connect to a secure network or other secure wireless communication and transfer encrypted IGS medical procedure data to a physician device, a hospital system device, or other device. After validation, the physician device or other device may decrypt and display the data. The transfer module may be useful for IGS navigation systems having no preexisting wireless capabilities; and for those having wireless capabilities that are less secure than those provided by the modified IGS navigation system. The transfer module may also wirelessly transmit IGS medical procedure data to a cloud storage system for subsequent access by end users.

19 Claims, 6 Drawing Sheets

(51) Int. Cl.
    *A61B 90/00*    (2016.01)
    *H04L 29/06*   (2006.01)
    *H04L 9/08*     (2006.01)
    *H04L 9/32*     (2006.01)
    *G16H 70/20*   (2018.01)
    *H04W 12/033*  (2021.01)
    *A61B 34/20*   (2016.01)

(52) U.S. Cl.
    CPC .......... *H04L 9/0894* (2013.01); *H04L 9/3226* (2013.01); *H04L 63/0471* (2013.01); *H04L 63/0876* (2013.01); *H04L 63/0884* (2013.01); *H04W 12/06* (2013.01); *A61B 34/20* (2016.02); *A61B 2034/2074* (2016.02); *H04L 2209/80* (2013.01); *H04L 2209/88* (2013.01)

(58) Field of Classification Search
    CPC ..... G16H 70/20; H04L 9/0891; H04L 9/0894; H04L 9/3226; H04L 63/0471; H04L 63/0876; H04L 63/0884; H04L 2209/80; H04L 2209/88
    See application file for complete search history.

(56) References Cited

U.S. PATENT DOCUMENTS

| | | | |
|---|---|---|---|
| 8,320,711 B2 | 11/2012 | Altmann et al. | |
| 8,702,626 B1 | 4/2014 | Kim et al. | |
| 8,874,453 B2* | 10/2014 | Menschik | G16H 70/20 705/3 |
| 10,146,961 B1* | 12/2018 | Baruch | H04L 9/14 |
| 2007/0232885 A1* | 10/2007 | Cook | G16H 30/40 600/407 |
| 2009/0262109 A1 | 10/2009 | Markowitz et al. | |
| 2009/0326985 A1* | 12/2009 | Martin | G16H 15/00 705/3 |
| 2010/0167334 A1 | 7/2010 | Williamson, IV | |
| 2011/0060214 A1 | 3/2011 | Makower | |
| 2011/0123027 A1* | 5/2011 | Gotthardt | G06F 21/6209 380/270 |
| 2011/0307947 A1* | 12/2011 | Kariv | H04L 63/08 726/9 |
| 2012/0140923 A1* | 6/2012 | Lee | H04L 9/0894 380/45 |
| 2013/0006867 A1* | 1/2013 | Dove | H04L 9/083 705/51 |
| 2013/0177157 A1* | 7/2013 | Li | H04L 9/08 380/277 |
| 2013/0191647 A1* | 7/2013 | Ferrara, Jr | G06F 21/6245 713/186 |
| 2014/0156988 A1* | 6/2014 | Takahashi | H04L 9/321 713/155 |
| 2014/0188513 A1 | 7/2014 | Balignasay et al. | |
| 2014/0276056 A1 | 9/2014 | Ohta et al. | |
| 2014/0364725 A1 | 12/2014 | Makower | |
| 2015/0046192 A1* | 2/2015 | Raduchel | G16H 10/65 705/3 |
| 2015/0248526 A1* | 9/2015 | Choi | G16H 40/20 705/2 |
| 2015/0278444 A1* | 10/2015 | Westin | G16H 30/40 382/128 |
| 2015/0310188 A1* | 10/2015 | Ford | H04L 63/0428 726/28 |
| 2015/0347682 A1* | 12/2015 | Chen | G16H 50/20 705/2 |
| 2016/0063187 A1* | 3/2016 | Vettrival | G06F 21/6245 705/51 |
| 2016/0234176 A1* | 8/2016 | Chu | H04L 63/06 |
| 2016/0310042 A1 | 10/2016 | Kesten et al. | |
| 2016/0310077 A1 | 10/2016 | Hunter et al. | |
| 2017/0011174 A1* | 1/2017 | Higgs | G16H 10/60 |
| 2017/0230871 A1* | 8/2017 | Rangaswamy | H04W 36/0033 |
| 2017/0257214 A1* | 9/2017 | Stufflebeam | H04L 9/088 |
| 2017/0262585 A1* | 9/2017 | Grow | G16H 10/60 |
| 2017/0293718 A1* | 10/2017 | Perez | G16H 10/65 |
| 2018/0131573 A1* | 5/2018 | Matsuda | H04L 43/0817 |
| 2018/0268164 A1* | 9/2018 | Minami | G06F 21/64 |
| 2019/0198138 A1* | 6/2019 | Baldwin | G06F 16/345 |
| 2019/0356479 A1* | 11/2019 | Grimme | H04L 9/14 |
| 2019/0386814 A1* | 12/2019 | Ahmed | H04L 9/3013 |

OTHER PUBLICATIONS

International Search Report and Written Opinion dated Aug. 16, 2019 for International Application No. PCT/IB2019/053530, 12 pages.

European Communication dated Aug. 18, 2021, for Application No. 19730212.8, 8 pages.

International Preliminary Report on Patentability dated Nov. 10, 2020, for International Application No. PCT/IB2019/053530, 9 pages.

* cited by examiner

MEDICAL IMAGE TRANSFER SYSTEM

PRIORITY

This application claims priority to U.S. Provisional Pat. App. No. 62/668,473, entitled "Medical Image Transfer System", filed May 8, 2018, the disclosure of which is incorporated by reference herein.

BACKGROUND

Image-guided surgery (IGS) is a technique where a computer is used to obtain a real-time correlation of the location of an instrument that has been inserted into a patient's body to a set of preoperatively or intraoperatively obtained images (e.g., a CT or MRI scan, 3-D map, etc.), such that the computer system may superimpose the current location of the instrument on the preoperatively obtained images. In some IGS procedures, one or more digital images (e.g., still images and/or video images) of the operative field is/are obtained. This may include a digital tomographic scan (e.g., CT or MRI, etc.) of the operative field that is obtained prior to surgery. In addition, or in the alternative, the digital images may be obtained via ultrasound or diagnostic catheters, fluoroscopy, and/or using other devices and techniques. A specially programmed computer is used to convert the digital tomographic scan data and/or other image data into a digital map. During surgery, a special medical instrument (e.g., catheter, guidewire, etc.) having a sensor (e.g., one or more coils that are responsive to externally generated electromagnetic fields) mounted thereon is used to perform the medical procedure while the sensor sends signals to the computer indicating the current position of the associated medical instrument. The computer correlates the data it receives from the instrument-mounted sensor with the digital map that was created from the preoperative tomographic scan. The tomographic scan images are displayed on a video monitor along with an indicator (e.g., crosshairs or an illuminated dot, etc.) showing the real-time position of the medical instrument relative to the anatomical structures shown in the scan images. In this manner, the surgeon is able to know the precise position of each sensor-equipped medical instrument by viewing the video monitor even if the surgeon is unable to directly visualize the medical instrument itself at its current location within the body.

An example of an electromagnetic IGS systems that may be used in cardiac electrophysiology is the CARTO® 3 System by Biosense-Webster, Inc., of Irvine, Calif. When applied to various procedures such as catheter ablation, endoscopic surgery, stereotactic surgery, and other minimally invasive procedures, the use of IGS systems allows the surgeon to achieve more precise movement and positioning of the surgical instruments than can be achieved without. As a result, IGS systems may be particularly useful during performance of various procedures where direct visibility of the surgical site is not possible (e.g., within the cardiovascular system), and even where limited visibility is possible through the use of an endoscope or other device.

While several systems and methods have been made and used with respect to IGS systems, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The inventors have conceived of novel technology that, for the purpose of illustration, is disclosed herein as applied in the context of image guided surgery. While the disclosed applications of the inventors' technology satisfy a long-felt but unmet need in the art of image guided surgery, the inventors' technology is not limited to being implemented in the precise manners set forth herein but could be implemented in other manners without undue experimentation by those of ordinary skill in the art in light of this disclosure. Accordingly, the examples set forth herein should be understood as being illustrative only and should not be treated as limiting.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Image Guided Surgery Navigation System

Figure 1:
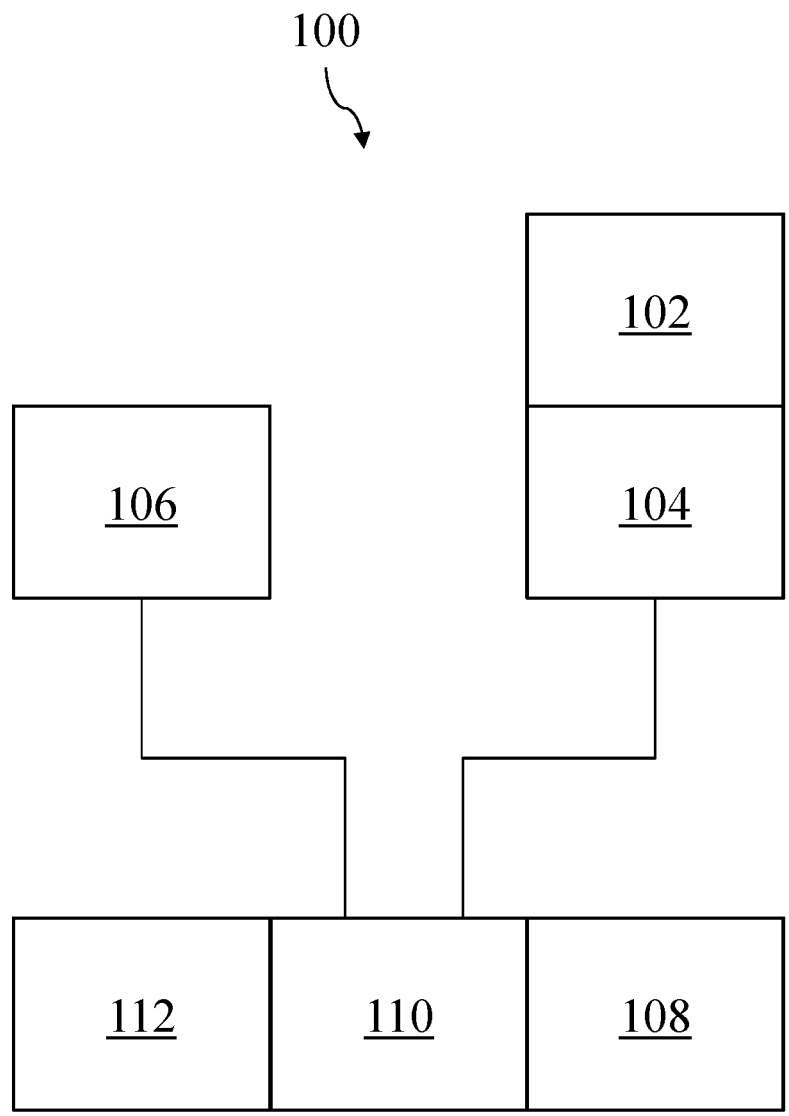
FIG. 1 depicts a schematic view of an exemplary image guided surgery navigation system.

FIG. 1 shows an exemplary IGS navigation system (100) enabling a procedure to be performed using image guidance. IGS navigation system (100) may be used with a variety of medical instruments (102) and other devices. In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 7,720,521, entitled "Methods and Devices for Performing Procedures within the Ear, Nose, Throat and Paranasal Sinuses," issued May 18, 2010, the disclosure of which is incorporated by reference herein; U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pub. No. 2016/

0310042, entitled "System and Method to Map Structures of Nasal Cavity," published Oct. 27, 2016, issued as U.S. Pat. No. 10,362,965 on Jul. 30, 2019; and U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein.

IGS navigation system (100) of the present example comprises a medical instrument (102) (e.g., a catheter) that is equipped with one or more position sensors (104), a field generator (106), and a processor (110). By way of example only, medical instrument (102) may comprise a catheter that is sized and configured to fit within a cardiovascular anatomical structure and provide a therapeutic effect (e.g., ablation on the anatomical structure). By way of further example only, each position sensor (104) may comprise a one wire coil or a plurality of wire coils that are configured to generate electrical signals in response to the presence of an alternating electromagnetic field; and/or in response to movement within a static magnetic field. In versions with two or more wire coils forming position sensor (104), the two or more wire coils may be oriented along respective axes that are orthogonal to each other or have any other suitable relationship with each other.

Field generator (106) of the present example is configured to generate an alternating electromagnetic field around at least a portion of a patient. By way of example only, field generator (106) may be integrated into a pad that is positioned under a patient. Alternatively, field generator (106) may take any other suitable form. A position sensor (104) in a medical instrument (102) may generate electrical signals when the portion of instrument (102) that is equipped with position sensor (104) is placed in or near the patient, within the electromagnetic field generated by field generator (106). The signals generated by position sensor (104) may be indicative of the position of position sensor (104) within the three-dimensional space of the electromagnetic field; and may thus be indicative of the position of the portion of instrument (102) that is equipped with position sensor (104) (e.g., the distal end of instrument (102)) within the three-dimensional space of the electromagnetic field. If the position of the patient within the three-dimensional space of the electromagnetic field is known, then the position of the portion of instrument (102) that is equipped with position sensor (104) within the three-dimensional space of the patient's anatomy may be derived based on signals from position sensor (104). Other techniques that may be used to generate real-time position data associated with a portion of medical instrument (102) may include wireless triangulation, acoustic tracking, optical tracking, inertial tracking, and the like.

Processor (110) of the present example comprises a computer processor or other processing unit communicating with one or more memories. Processor (110) uses software stored in a memory of processor (110) to calibrate and operate system (100). Processor (110) is in communication with position sensor (104) such that processor (110) may receive and process the position-indicative signals generated by position sensor (104). Processor (110) may communicate with position sensor (104) via wires, wirelessly, or in any suitable fashion as will be apparent to those of ordinary skill in the art in view of the teachings herein. Processor (110) is also in communication with field generator (106), such that processor (110) is operable to selectively activate field generator (106) to thereby generate the electromagnetic field. A set of operating controls (112) are also in communication with processor (110). Operating controls (112) may comprise a keypad, a pointing device such as a mouse or trackball, and/or any other suitable kind(s) of user input feature(s) as will be apparent to those of ordinary skill in the art in view of the teachings herein. A physician may use operating controls (112) to interact with processor (110) while performing the surgical procedure.

A display screen (108) is coupled with processor (110) and is operable to render images of patient anatomy. Such images may be based on a set of preoperatively obtained images (e.g., a CT or MRI scan, 3-D map, etc.). The views of patient anatomy provided through display screen (108) may also change dynamically based on signals from position sensor (104). For instance, as medical instrument (102) moves within the patient, the corresponding position data from position sensor (104) may cause processor (110) to update the patient anatomy views in display screen (108) in real time to depict the regions of patient anatomy around the portion of medical instrument (102) that contains position sensor (104).

Moreover, processor (110) may drive display screen (108) to superimpose the current location of medical instrument (102) on the preoperatively obtained images of the patient's anatomy, such as by superimposing an illuminated dot, a crosshair, a graphical representation of medical instrument (102), or some other form of visual indication. Such a superimposed visual indication may also move within the images of the patient anatomy on display screen (108) in real time as the physician moves medical instrument (102) within the patient, thereby providing real-time visual feedback to the operator about the position of medical instrument (102) within the patient. The images provided through display screen (108) may thus effectively provide a video tracking the position of medical instrument (102) within a patient, without necessarily having any optical instrumentation (i.e., cameras) viewing the portion of medical instrument (102) that is in the patient. Nevertheless, in scenarios where the operator is also using an endoscope or other kind of optical instrumentation, the endoscopic/optical image may also be provided on display screen (108). The images provided through display screen (108) may ultimately help guide the operator in maneuvering and otherwise manipulating instruments during a procedure.

II. Exemplary Medical Image Transfer System

Some forms of IGS navigation system (100) may store a variety of data types during an IGS procedure, including information and analytics describing the IGS procedure, still images produced or captured during the IGS procedure, video sequences produced or captured during the IGS procedure, and other data. Such stored information may further include recordings of all data collected during the entire IGS procedure, which may be referred to as a "full case recording." At least some of the data stored by an IGS navigation system (100) may be subsequently needed for various reasons, such as when a patient may wish to retain images or video associated with a procedure for future treatment; or when a physician may wish to review images, video, or other information related to a procedure to formulate a diagnosis or subsequent plan of care.

Some forms of IGS navigation system (100) may have somewhat limited capabilities to communicate data to other systems and devices, with some being incapable of wireless communication using technologies such as Bluetooth, Wi-Fi, NFC, RFID, cellular, or other similar technologies. Some forms of IGS navigation system (100) (e.g., those that are not networked within a hospital) may also be incapable of wired communication. In some versions of IGS navigation system (100) that are incapable of wired or wireless communication, it may be necessary to physically retrieve data from IGS navigation system (100), such as by printing physical copies of images or information, producing optical data discs such as CD-ROM or DVD-ROM with an optical drive of the system, or reproducing data from the IGS system to a physically connected storage device such as a USB hard drive or USB flash drive. Such data transfer procedures may have a variety of drawbacks and limitations. For example, producing printed papers and optical data discs may be very time consuming and relatively expensive in terms of materials and resources. Reproducing data to physically connected storage devices may also be time consuming depending on a variety of factors; but may also be relatively costly if such storage devices must be purchased and made readily available to physicians and patients. Physical reproductions of data, whether on paper, disc, or storage device, may also present a risk of losing or misplacing the physical reproduction, which could expose the potentially confidential and sensitive medical data thereon to public disclosure. Moreover, these conventional data transfer procedures to printed papers, optical data disks, and physically connected storage devices may lack automated encryption or other forms of substantial data protection.

Some forms of IGS navigation system (100) may also represent a significant capital investment for a hospital or other medical practice. As a result, it may be undesirable to replace a preexisting IGS navigation system (100) with a new form of IGS navigation system (100) that includes enhanced data communication capabilities. It may instead be desirable to provide features that further facilitate the transfer of data from a preexisting IGS navigation system (100) without requiring replacement of the preexisting IGS navigation system (100). In other words, it may be desirable to provide a retrofit for a preexisting IGS navigation system (100) to thereby provide enhanced data transfer capabilities to the preexisting IGS navigation system (100). An example of such a retrofit is described in greater detail below. While the following example is described in the context of retrofitting a preexisting IGS navigation system (100), the same enhanced data communication features may also be provided with a new IGS navigation system (100), such that the preexisting status of IGS navigation system (100) is not required in order for the following example to be carried out in practice.

Figure 2:
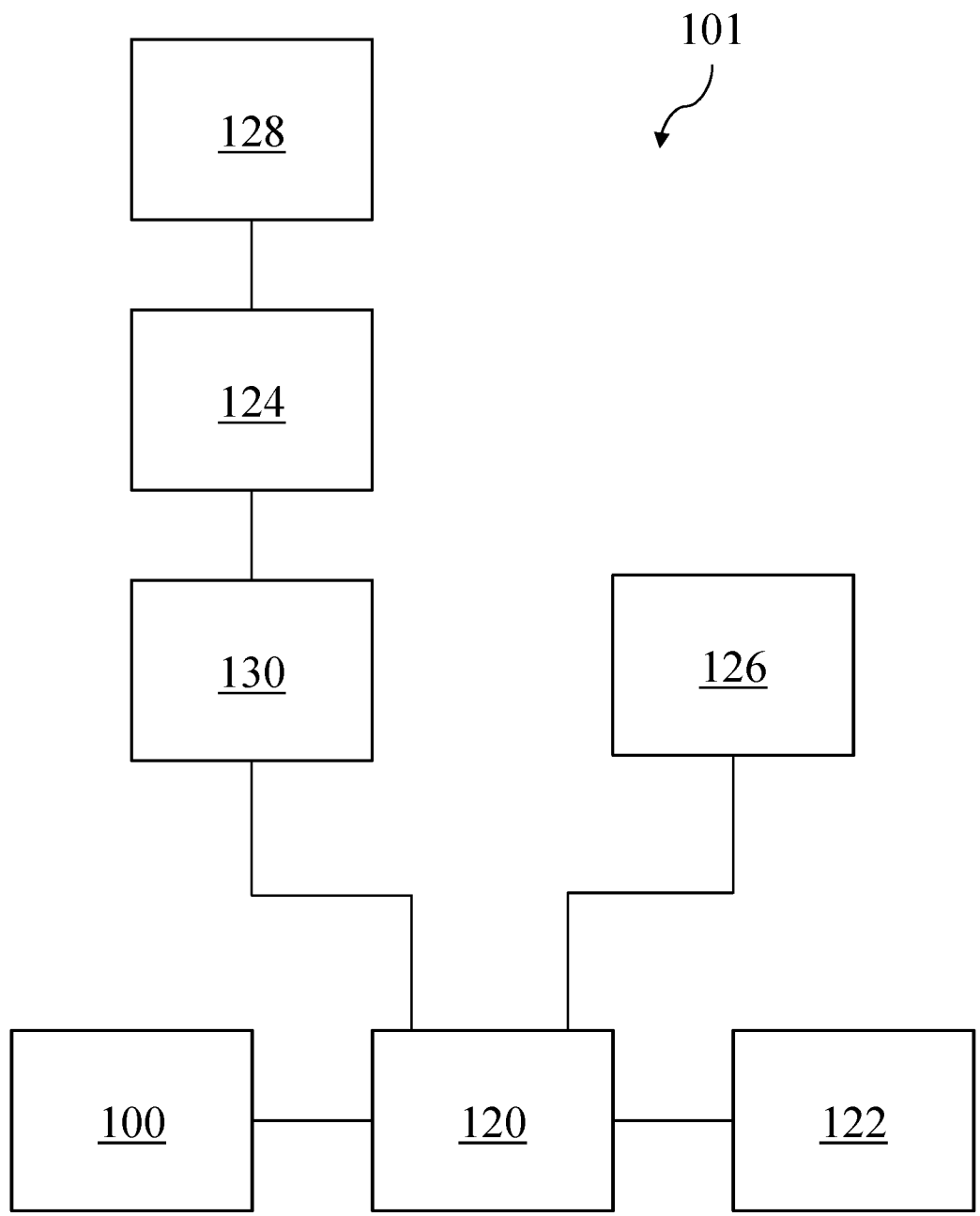
FIG. 2 depicts a schematic view of an exemplary data transfer system including the image guided surgery navigation system of FIG. 1.

FIG. 2 shows a schematic diagram of a data transfer system (101) that is configured to allow data, such as images, video, and procedural information, that is captured or produced by IGS navigation system (100) to be wirelessly and securely accessed by users even where IGS navigation system (100) does not have wireless communication capabilities; or where the IGS navigation system (100) has wireless communication capabilities that are not appropriate for secure wireless access to potentially sensitive and confidential patient data.

Figure 3:
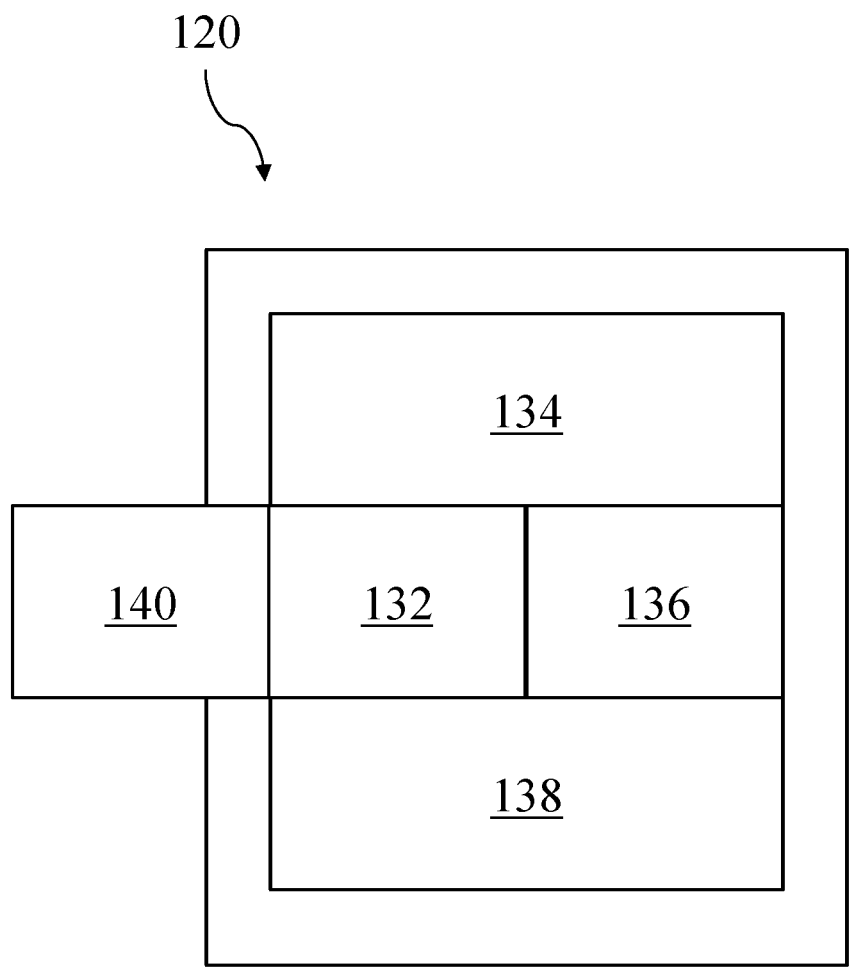
FIG. 3 depicts a schematic view of an exemplary transfer module of the data transfer system of FIG. 2.

In the example shown in FIG. 2, IGS navigation system (100) is communicatively coupled with a transfer module (120) via a physical connection such as a USB port, ethernet port, serial port, parallel port, or other standard or proprietary physical connection that allows for the exchange of data between two or more devices. IGS navigation system (100) is configured to export images, video, and other data to a physically connected storage device through this connection. Transfer module (120), shown in more detail in FIG. 3, is configured to appear to processor (110) as a physically connected storage device (e.g., as a USB connected flash drive or hard drive) and securely receive procedure data and images from IGS navigation system (100) during export of such data. Transfer module (120) is configured to securely store received data, and to wirelessly provide some or all of that data to requesting devices that can be authenticated and verified.

A transfer server (122) is configured to allow administrative users to maintain user and device authorization and verification records, and to maintain and provide software configuration and software updates to one or more transfer modules (120). The transfer server (122) may provide configurations to the transfer module (120) wirelessly via the same wireless communication devices and networks used to provide images and data to users, via a network using a fixed physical connection such as USB or ethernet, or via a manual process such as copying configurations from the transfer server (122) to physical storage devices such as USB flash drives which may be temporarily connected to IGS navigation system (100).

Transfer module (120) of the present example is wirelessly coupled with devices such as a trusted user device (126) and a new user device (124). By way of example only, user devices (124, 126) may comprise smartphones, tablets, laptops, or other devices having software configurations and hardware features that allow for the secure exchange of data with transfer module (120). User devices (124, 126) may also include mobile or fixed-location workstations within a hospital. Other suitable forms that user devices (124, 126) may take will be apparent to those of ordinary skill in the art in view of the teachings herein. Trusted user device (126) of the present example is a device that is recognized by transfer module (120) as already being configured and authenticated for secure access to some or all of the data received from IGS navigation system (100). New user device (124) of the present example is a device that is not recognized by the transfer module (120) because it is either a device that has not yet been authenticated or a device that was previously authenticated but whose authentication has expired or changed in some way.

New user device (124) is also in wireless communication with a validation server (128), which may the be same or a separate device as transfer sever (122), that is configured to determine whether new user device (124) should be granted access to one or more images or other data on transfer module (120) based upon information from one or more of new user device (124), transfer server (122), or transfer module (120). In some implementations, trusted user device (126) and new user device (124) communicate with transfer module (120) using basic features of their operating system or standard software; while in other implementations, communication with the transfer module (120) is performed using a specialized software application that is installed and executed on device (124, 126) for the purpose of receiving data from the transfer module (120).

While unrelated to whether a particular device (124, 126) is trusted or not trusted, FIG. 2 also shows that the transfer module (120) may be in communication with trusted user device (126) (or, in other cases, new user device (124)) directly and without a typical network connection via a wireless communication such as Bluetooth or Wi-Fi Direct. Such connections may allow a physician or patient to transfer data from transfer module (120) immediately or shortly after a procedure while they are still in somewhat close proximity to IGS navigation system (100) and the connected transfer module (120). Transfer module (120) is also capable of communication with a device such as new user device (124) (or, in other cases, trusted user device (126)) via a wireless connection to a wireless local area network or wide area network such as the network (130). Such connections may allow a physician or patient to transfer data from transfer module (120) while located an area where they can connect to the network (130) in the case of a local area network; or, in implementations where network (130) is a wide area network, from their own home, another doctor's office, or any other location having access to the wide area network (130).

In some implementations, providing network (130) in the form of a local area network may advantageously provide an increased level of data security by preventing general access from across a wide area network; and may also allow for transfer modules (120) to be configured to only communicate across dedicated local area networks having unique or hidden network names and passwords that are only provided to a small set of users needing to access IGS navigation system (100) data. Unique dedicated networks could be shared across one or more transfer modules (120) or could be uniquely designated on a per-transfer module (120) basis to further compartmentalize network (130).

In addition to the use of a wireless local and wide area networks (130), the data transfer described herein may also be carried out via cellular connections (e.g., 4G, 5G, etc.). Moreover, such cellular and other wireless connections may be used to communicate data to an offsite cloud storage system, from which user devices (124, 126), servers on site at a hospital or other facility, and/or other devices may later access the data. In other words, while the arrangement shown in FIG. 2 provides a direct path of communication between user device (124) and transfer module (120) via network (130), some other arrangements may provide a cloud storage system as an intermediary between transfer module (120) and user device (124), with transfer module (120) being in communication with the cloud storage system via a network (e.g., network (130), a cellular data connection, etc.); and with user device (124) being in communication with the cloud storage system via a network (e.g., network (130), a cellular data connection, etc.). The cloud storage system may be located remotely from the hospital or other facility in which IGS navigation system (100) and transfer module (120) are situated. As described herein, the data sent from transfer module (120) to the cloud storage system may be encrypted, and such encryption may be maintained when the data is transferred from the cloud storage system to the user device (124), with the user device (124) decrypting the data. This same arrangement may be used to provide data from the cloud storage system to any user devices (124, 126) (e.g., mobile devices or hospital workstations, etc.), servers on site at a hospital or other facility, and/or other devices.

FIG. 3 shows a schematic diagram of exemplary components of transfer module (120). As can be seen, transfer module comprises a processor (132) that is capable of receiving and transmitting data, processing data, and executing software. Processor (132) is in communication with a memory (134) that is capable of storing and accessing data in use by the processor (132). Transfer module (120) also comprises a storage device (136) for storing data received from IGS navigation system (100), storing configurations related to user access and validation, device access and validation, performance and execution of various tasks and maintenance of the transfer module (120), and other data. By way of example only, storage device (136) may comprise a flash memory device such as a USB flash memory drive, an SD card, or any other suitable kind of storage device.

Transfer module (120) also comprises a communication device (138), which may comprise one or more of a wireless transceiver for Bluetooth, Wi-Fi, RFID, NFC, cellular data, and/or other appropriate wireless communication technology. Transfer module (120) further includes an IGS system interface (140), which may comprise a USB connection, ethernet connection, or other physical or mechanical connection that allows transfer module (120) to be coupled with IGS navigation system (100) for data transfer.

By way of example only, transfer module (120) may comprise a single board computer ("SBC"), such as a RASPBERRY PI® device by Raspberry Pi Foundation of Cambridge, United Kingdom, having capabilities such as Wi-Fi and partitions for USB mass storage and/or SD card mass storage; and being configured for secure HTTP ("HTTPS") communications with local secure socket layer ("SSL") with a self-signed certificate, server-side execution of all programming and scripts using a secure scripting framework, such as Node JS and Express Server, scripts to manage wireless connections, device authentications, file encryption, audit logs, and file clean up, and static network configurations. In some versions where transfer module (120) comprises a RASPBERRY PI® device, transfer module (120) may couple with IGS navigation system (100) via USB coupling; and may wirelessly transfer data from IGS navigation system (100) via Wi-Fi. In some such versions, transfer module (120) couples with a USB port of IGS navigation system (100) that would otherwise be used to transfer images and other data from IGS navigation system (100) to a flash drive or other USB storage device. Other appropriate devices and configurations that may be used to provide transfer module (120) will be apparent to one of ordinary skill in the art in view of the teachings herein.

III. Exemplary Medical Image Transfer Method

Figure 4:
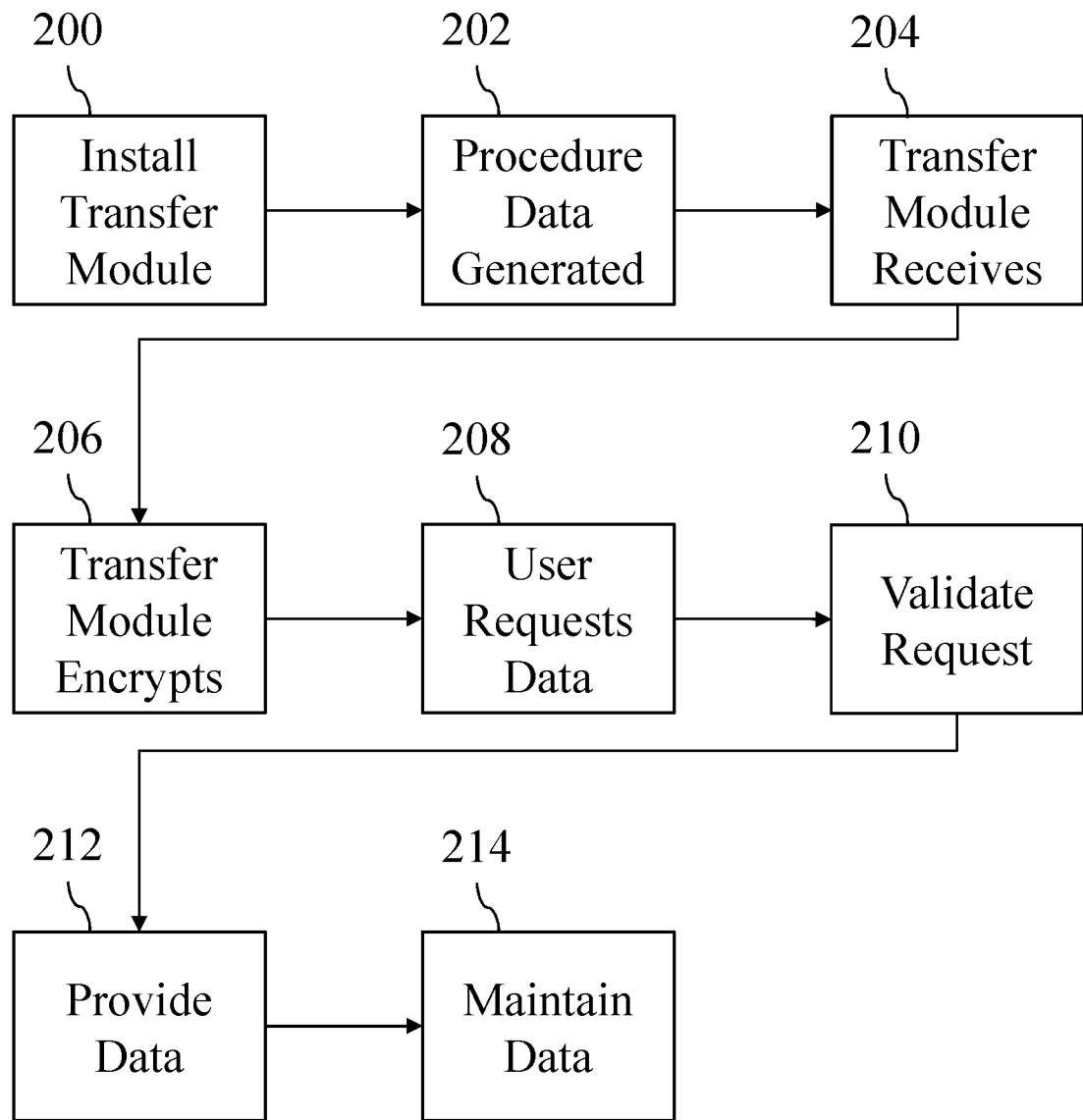
FIG. 4 depicts a set of high level steps that may be performed by the data transfer system of FIG. 2 to securely transfer data.

FIG. 4 shows an exemplary set of high level steps that the data transfer system (101) could perform to provide improved data transfer capabilities for users of IGS navigation system (100). Initially, transfer module (120) may be installed (block 200) on IGS navigation system (100) and configured for use. In some implementations, transfer module (120) may be manually configured by an administrator before installation; while in other implementations, transfer module (120) may be automatically configured by transferring a set of configuration data to transfer module (120) via IGS system interface (140) or another interface. Transfer module (120) may, upon initial boot up or at regular intervals, check for configuration information and execute changes when it is detected. Configurations provided to transfer module (120) may include Wi-Fi configurations (e.g., SSID, password), network configurations (e.g., predefined static IP address and port), file system configurations (e.g., space allocated for data from IGS navigation system (100), data refresh interval, data retention policies), encryption and security settings (e.g., HTTPS configurations, SSL certificate, SHA/RSA keys), local audit log parameters (e.g., types of activities logged, user audit setup, log size and retention), and other settings.

As medical procedure data is generated (block 202) during a medical procedure performed with the aid of IGS navigation system (100), images, video, and/or other information may be generated and stored on the IGS navigation system (100). With transfer module (120) installed (block 200) and configured for use, at least some of the data generated (block 202) during a medical procedure will be transmitted from IGS navigation system (100) and received (block 204) by transfer module (120) by being pushed at configurable intervals, pulled upon request, or both. Data received (block 204) by transfer module (120) will be encrypted (block 206), including both the data itself as well as filenames and any associated metadata, and stored on storage device (136) of transfer module (120) so that it is not readily accessible by someone having physical access to the transfer module (120).

A user may request (block 208) some or all of the stored data from the transfer module (120) by using a properly configured user device such as new user device (124) or trusted user device (126). Requesting (block 208) data may be performed through a web browser or other feature integrated into the operating system of the requesting user device or may performed through a software application provided by administrators of the transfer module (120) and installed on the user device. Requests (block 208) may be performed on a schedule (e.g., automatically at he start or end of a day) or may be performed on demand (e.g., immediately after completion of a medical procedure, etc.), or at other times or schedules as desired. As another merely illustrative example, requests (block 208) may be performed on an ad hoc basis during a medical procedure. For instance, transfer module (120) may provide intra-procedure data transfers for the operating surgeon to receive clinical feedback from colleagues, thought leaders, etc., during the medical procedure. As yet another merely illustrative example, requests (208) may be performed during or after a medical procedure to provide data to a hospital electronic medical record (EMR), for purposes of being included within the patient's procedural notes and/or medical record. Other scenarios in which it may be desirable to provide a request (block 208) for medical procedure data will be apparent to those of ordinary skill in the art in view of the teachings herein.

When transfer module (120) receives a request (block 208) for medical procedure data, the request will be validated (block 210) before any information is provided. Validation (block 210) may include one or more of user validation (e.g., authenticating a user based upon a username and password, biometric authentication, or other similar methods) and user device (124, 126) validation (e.g., verifying that user device (124, 126) from which a request originated has a security device such as a token or certificate, MAC address or unique device address verification, or other similar methods), and may also include administrative or legal validation steps. This could include, for example, providing a request to a third party to be manually reviewed and approved before data is provided, determining whether the requester has a valid reason to request the particular data (e.g., based upon being listed as a care provider for the associated patient, or based upon being employed in a certain position or role that requires the data), or ensuring that the requester has agreed to maintain the data confidentially (e.g., capturing a signature, password, biometric identifier, or image of a user of the requesting device and associating that with acceptance of a set of legal terms and conditions for receiving the requested data).

As described herein, biometric identification may include the creation of unique keys based upon a particular user's face, fingerprint, voice, or other capturable biometric input. Such unique keys may be used to authenticate access to the transfer module (120), user devices (124, 126), or other devices of the data transfer system (101), and may also be used, in whole or in part, as part of an encryption/decryption key for data stored or accessed on any such device. Such examples may include storing user credentials for the user device (126) in an encrypted format, where biometric data provides the decryption key and allows the user device (126) to communicate with the transfer module (120), or may include the user device (126) receiving encrypted procedure data (e.g., pre- or post-operative images) from the transfer module (120), and decrypting that data for viewing using a decryption key based wholly or partially on biometric data associated with a particular patient authorized to have access to such data, or a particular physician authorized to have access to such data, or other variations on such examples.

Once a request is validated (block 210), transfer module (120) may provide (block 212) the requested data via the configured wireless connection. Providing data (block 212) may include providing some or all of the data during one or more exchanges. For example, transfer module (120) may first provide (block 212) a list of file names, patient names, physician names, or procedure names associated with data currently stored on transfer module (120). Based upon an additional request from the user of one or more of the listed files, transfer module (120) may then provide requested files themselves. Whether file names or actual files, data provided (block 212) wirelessly will be encrypted during transit and only decrypted after receipt by an authorized device (124, 126). Providing (block 212) the requested data may be performed in a variety of ways. For example, in some versions, the data may be provided by a web server running on transfer module (120) via HTTP with anonymous authentication. Such a web server may be customized to provide only the functions required for transmitting files to the requesting user, such as disabling or prohibiting common web server functions such as POST, PUT and DELETE, and other changes to improve security, to remove features which are unnecessary and may expose unintended functionality, and to prevent cross side scripting and other web server vulnerability attacks.

Other implementations may include a web server running on transfer module (120) and using HTTPS with a self-signed certificate and local SSL to provide the requested data. This may be paired with customized scripting or software installed on user device (124, 126) to automatically accept or ignore warnings related to the transfer module's (120) SSL certificate. Such an implementation could also use a customized web server providing only the bare set of functions to allow the data to be provided to user devices (124, 126) and may also include additional security features to prevent cross side scripting and other web server attacks, as well as automatic generation and renewal of local SSL certificates to avoid the need for manual creation and renewable of certificate over time.

Other implementations may be configured to email data to users instead of or in addition to providing data via HTTP or HTTPS. Emails may be produced based upon templates for each individual or for groups of users, such that emails provided to users may be customized for their preferences.

Data transfer system (101) may also be configured to perform data maintenance (block 214) tasks regularly. This could include causing IGS navigation system (100) to store or discard data based upon a set of retention rules, causing transfer module (120) to store or discard data based upon a set of retention rules, and/or causing the user devices (124, 126) to store or discard data based upon a set of retention rules. As an example, the transfer module (120) may be variably configured to apply file retention policies to storage on the storage device (136), this may include limiting the total amount of data stored at any one time, limiting the number of patients or procedures for which data is stored at any one time, limiting the number of days for which a particular set of data may be stored before automatic deletion, and other data retention rules. Such configurations may be statically configured by an administrator or manufacturer of the transfer module (120), or may be configured from time to time using a configuration change file, as will be described below.

Figure 5:
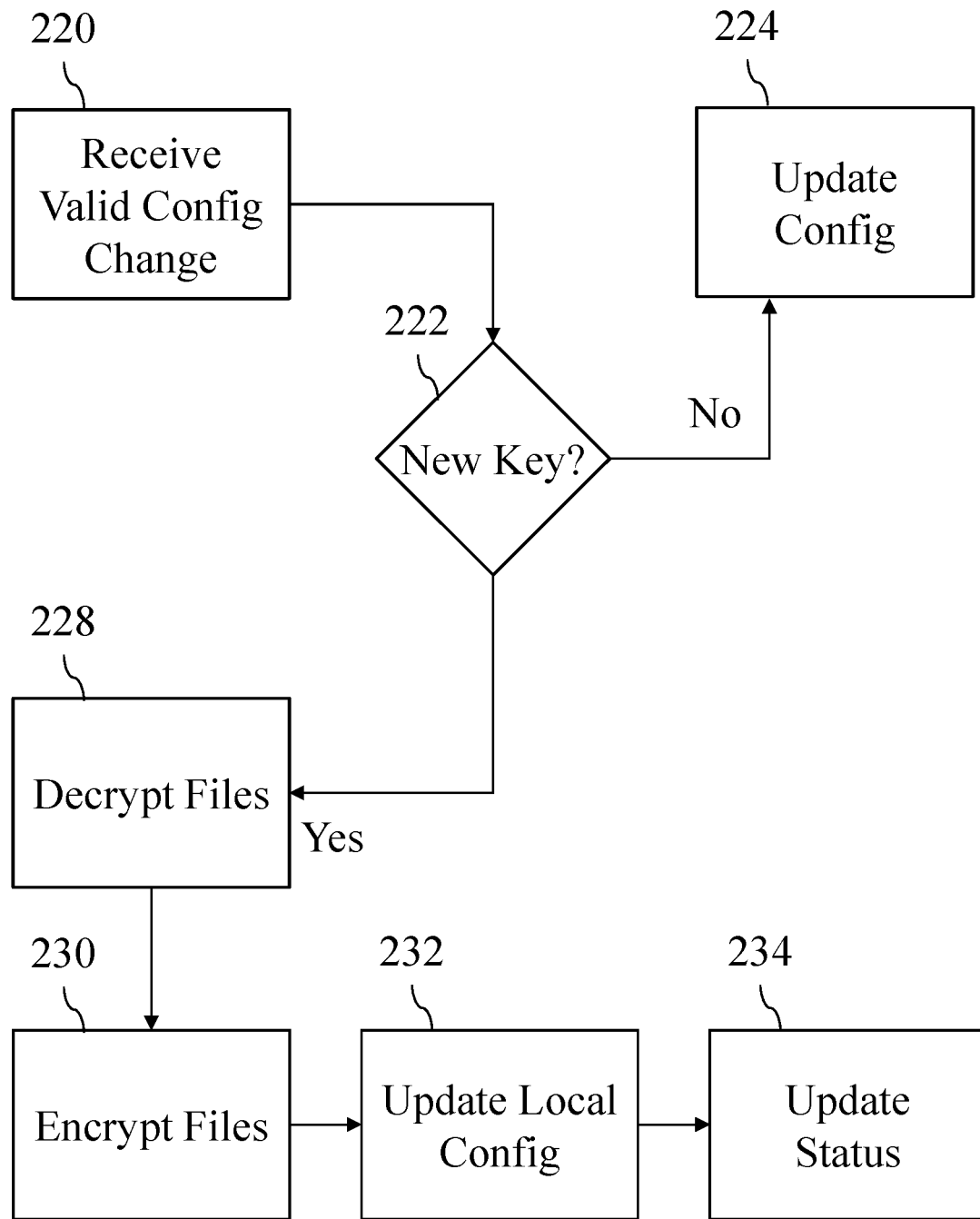
FIG. 5 depicts a set of steps that may be performed by the transfer module of FIG. 3 to update configurations.

FIG. 5 shows an exemplary set of steps that could be performed by transfer module (120) during configuration. These steps could be performed by an application or scripts executing on transfer module (120), which may regularly scan for configuration files that have been placed on or transmitted to transfer module (120). When a configuration change is received (block 220), transfer module (120) will determine the contents of the configuration change. This could include identifying new Wi-Fi configurations such as SSID and password, a new encryption/decryption key, a key change flag, as key version number, and other similar configuration changes, as well as the current encryption/decryption key, which can be used to verify the configuration change before it is executed. Transfer module (120) may confirm that the provided current encryption key is valid by decrypting a file as a test, and where it is determined to be valid, make the configuration changes. If the key is invalid, an error may be returned by updating the configuration file to reflect the occurrence of an error for subsequent viewers of the configuration file, or wirelessly transmitting an error notification.

Where the configuration changes are valid, but do not contain a positive key change flag (block 222), transfer module (120) may update its configurations (block 224) according to the provided configuration file or data; but will not make any changes related to encryption. Where the configuration changes do contain a positive key change flag (block 222), all files and data on transfer module (120) will be decrypted (block 228) using the current key from the configuration change, and then encrypted (block 230) using the new key from the configuration change. After decryption (block 228) and encryption (block 230) are successful, transfer module's (120) local configuration will be updated (block 232) based upon the configuration changes and the new key from the configuration change will be stored on transfer module (120) as the current key. Transfer module (120) may also update (block 234) a configuration status, which may include returning a notification to transfer server (122), generating a successful configuration change flag or file locally, or providing a perceptible notification via transfer module (120) itself. Such a perceptible notification may be provided in the form of a flashing light or other visual indicator, in the form of an audible confirmation, and/or in any other suitable form. Operating in the manner shown in FIG. 5, configuration changes to transfer module (120) may be securely updated by administrators of the system having physical access to transfer module (120); or access to network (130) to which transfer module (120) is connected.

Figure 6:
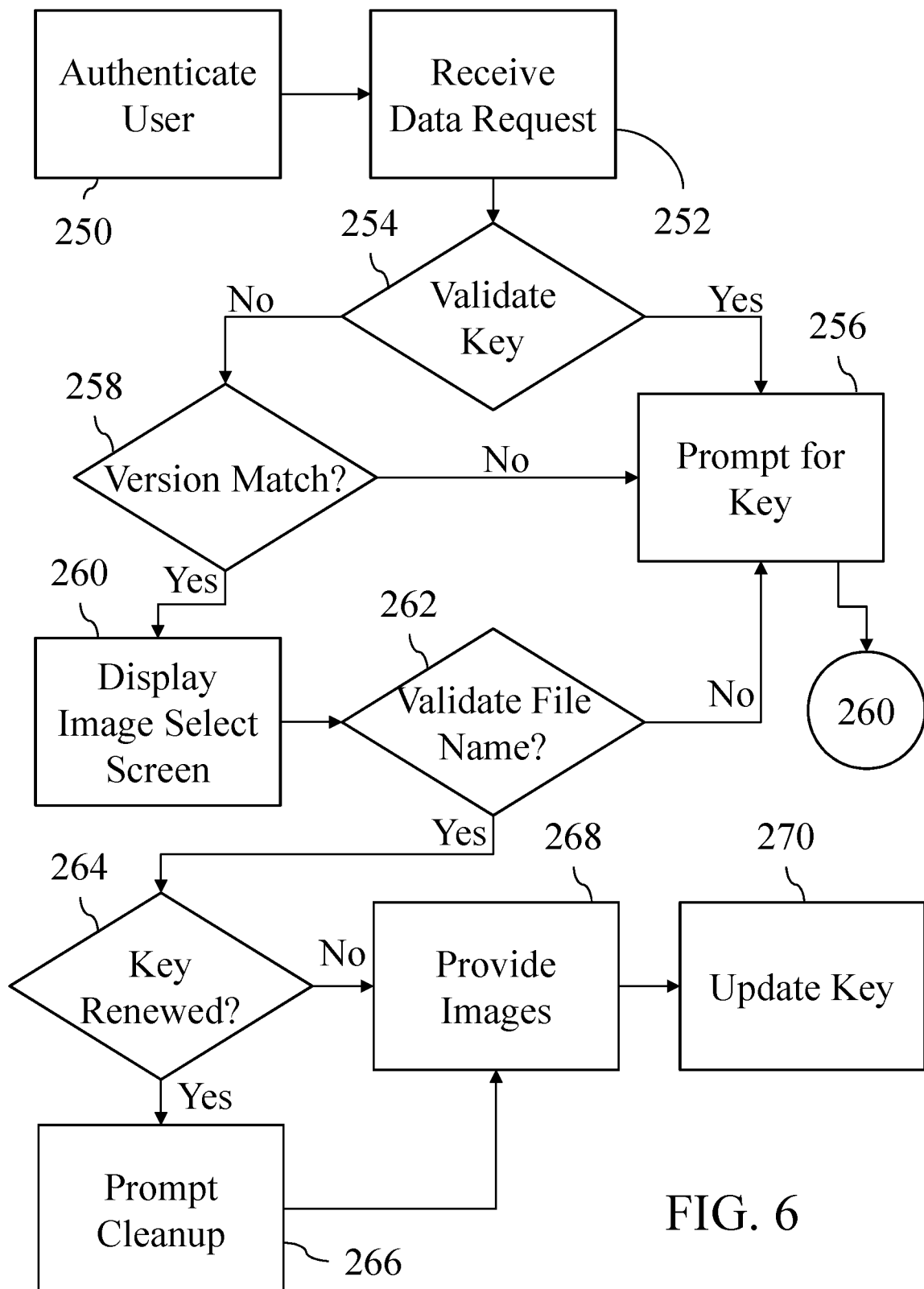
FIG. 6 depicts a set of steps that may be performed by the an appropriately configured user device to access and retrieve data from the transfer module of FIG. 3.

FIG. 6 shows a set of steps that could be performed by a user device such as new user device (124) to securely provide access to medical procedure data to a requesting user. In some implementations, the steps of FIG. 6 may be performed by a software application, such as an android, iOS, or Windows mobile application, which may be a native or hybrid application; or in some implementations a web site accessible via a web browser. Upon initially accessing this software, transfer module (120) will authenticate (block 250) the user based on a user name and password, biometric authenticator, or other similar authentication measure. User authentication may be performed by transfer module (120) in conjunction with one or more of transfer server (122) and validation server (128), which may be configured to store databases storing some or all of the authentication information needed to verify a user name and password or other authenticator.

Once a user has been authenticated (block 250), user device (124) may receive (block 252) a data request from a user of user device (124) via a user interface such as a touch screen, keyboard, or other interface. The data request may be, for example, a request for data associated with a particular IGS navigation system (100), or a particular patient, doctor, or procedure associated with one or more IGS navigation systems (100). Before acting upon the request, user device (124) will determine an encryption key and a MAC address based upon locally available information, communication with transfer module (120), or both, and use that information to validate (block 254) user device (124) for communication with transfer module (120). Validation (block 254) of user device (124) may be accomplished by, for example, querying a local databased that is bundled with user device (124) software and updated from time to time to determine whether a record exists in a mapping table that associates the devices unique MAC address with the encryption key. This database could be comprised of fields such as user device (124) MAC address or other unique identifier, an encrypted filename and decrypted filename that may be used to verify the effectiveness of the encryption key, transfer module (120) MAC address or other unique identifier, and a date and time of the records creation or entry into the database.

If the key cannot be validated (block 254) because, for example, there is no record uniquely associating user device (124) with the key, user device (124) will prompt (block 256) the user to enter a new encryption key. Similarly, if there is a record associating user device (124) with the key, but the key version from the local database does not match the current key version based upon information from transfer server (122) or validation server (128), user device (124) will prompt (block 256) the user to enter a new encryption key.

Where the key can be validated (block 254) and where the key version matches (block 258), or where a user is prompted (block 256) for a new key, user device (124) may then display (block 260) an image selection screen showing a set of file names associated with data stored on transfer module (120). This may be accomplished by, for example, receiving from transfer module (120) a set of file names, in an encrypted form, associated with the data request (block 252). The set of file names may be stored on user device (124) in an encrypted format, with decrypted versions being created and stored only temporarily for the purposes of validating encryption keys, and immediately before providing (e.g., by email to a secured account using an email template, within a secure application or browser session, or otherwise) the decrypted images or other data to a requester after all validation steps are complete.

User device (124) may prompt the user to confirm one or more of the file names to verify that the correct data has been identified on transfer module (120) and that the user is authorized to access it, and may validate (block 262) one or more of the file names, thumbnails or other information by using the key to decrypt the data and examining the results. This could include, for example, selecting an encrypted file name present in a record of the local database, decrypting the file name with the encryption key, and comparing the result to the decrypted file name also stored in the local database. If user device (124) cannot validate (block 262)

that the file name decrypted correctly, the user may be prompted (block 256) for a new key.

If user device (124) is able to validate (block 262) the filename, user device (124) will determine whether the encryption key used throughout the steps of FIG. 6 was an initially valid key such as a new key being used for the first time or an old key whose version still matches the current key version, or whether the key was renewed (block 264) during the process by prompting (block 256) the user to enter a new key. Where the key was initially valid and did not need to be renewed (block 264), user device (124) may retrieve the requested images or data from the transfer module, decrypt them, and display or otherwise provide (block 268) the requested data to the user. Where the key was renewed during the process by prompting (block 256) the user to enter a new key, user device (124) will notify (block 266) the user that old files and data stored on user device (124) that are associated with an old encryption key that is no longer valid (e.g., due to version mismatch, failure to decrypt file name, or other reason) are being deleted and must be downloaded again if continued access is desired. This prevents a user device (124) from gathering different sets of files and data over time that each require different encryption keys to access. Once the user has been notified (block 266) of cleanup and other maintenance relating to the renewed key (block 264), user device (124) may then provide (block 268) the requested files and data to the user.

Providing (block 268) the requested images or data to the user may include providing a preview to the user of the images, video, and other data associated with the request that are available on transfer module (120) in thumbnail or preview form. In some implementations, this may include using an HTTP or HTTPS call to the web server of transfer module (120) to get the full path of each associated image, video, or other data, and use those paths to render and display a preview web page in a browser window, native application, or hybrid application. Providing (block 268) the requested images or data may also include receiving an input via a user interface of user device (124, 126) indicating one or more of the previewed images or other data, and using an HTTP or HTTPS call to the web server of the transfer module (120) to download the indicated data to user device (124, 126) directly, where it may be stored in an encrypted form and only decrypted on demand when it is viewed by a user of user device (124, 126) or emailed to a secure email account associated with the authenticated user.

In any case, after user device (124) provides (block 268) data to the user, the local database may have a record created, inserted, or otherwise be updated (block 270) and associated with the unique hardware identifiers of user device (124) to describe the now completely validated encryption and decryption key, its version, and other validation information stored in the local database. As the local database is updated (block 270) it may regularly be synced with a similar database available on the transfer server (122), validation server (128), or another remote storage to reduce the number of validation steps that may be performed during the steps of FIG. 6 and provide users of user device (124, 126) more streamlined access.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A data transfer system comprising: (a) a transfer module comprising a storage device, a wireless communication device, and a data interface, wherein the data interface is configured to couple with and receive data from an image guided surgery navigation system, wherein the wireless communication device is configured to connect to a wireless network; (b) a transfer server configured to provide security and authentication services associated with access to the transfer module; and (c) a user device comprising a display and a user interface, wherein the user device is in communication with the transfer module over the wireless network; wherein the transfer module is configured to: (i) receive a set of medical procedure data from the image guided surgery navigation system, (ii) encrypt the set of medical procedure data as a set of encrypted medical procedure data using a current key, store the encrypted medical procedure data on the storage device, and delete the set of medical procedure data, (iii) receive a medical procedure data request from the user device, and (v) provide the set of encrypted medical procedure data to the user device

Example 2

The system of Example 1, wherein the user device is configured to: (i) store a device key and a device key version, (ii) authenticate a user of the user device, (iii) validate the user device based upon the device key and the current key, (iv) when the user device is not validated, prompt the user for a new key and set it as the device key, then delete any information on the user device associated with a previous device key, and (v) when the user device is validated, receive the set of encrypted procedure data and decrypt the set of encrypted procedure data using the device key.

Example 3

The system of Example 2, wherein the user device is further configured to: (i) receive a set of authentication data from the user, (ii) provide the authentication data to the transfer server, and (iii) authenticate the user based upon an authentication response from the transfer server.

Example 4

The system of any one or more of Examples 2 through 3, wherein the user device is further configured to: (i) store a local validation database comprising a unique hardware identifier, a file description, an encrypted file description, and a key version, wherein the file description and the encrypted file description both describe the same file, and wherein the encrypted file description is created from the file description using the device key, (ii) receive a module identifier and a module key version from the transfer module, and (iii) validate the user device when the local validation database contains a record whose key version matches the module key version and whose module identifier matches the unique hardware identifier.

Example 5

The system of any one or more of Examples 2 through 4, wherein the user device is further configured to: (i) receive a module key version from the transfer module, and (ii) validate the user device when the module key version matches the device key version.

Example 6

The system of any one or more of Examples 2 through 5, wherein the user device is further configured to: (i) store a local validation database comprising a file description and an encrypted file description, wherein the file description and the encrypted file description both describe a file stored on the transfer module, and wherein the encrypted file description is created from the file description using the device key, (ii) request a file portion associated with the encrypted file description from the transfer module, (iii) decrypt the file portion using the device key to create a decrypted file portion, and (iv) validate the user device where the decrypted file portion matches the file description.

Example 7

The system of any one or more of Examples 2 through 6, wherein the user device is further configured to: (i) select a set of encrypted file names from the set of encrypted medical procedure data, (ii) where the user is authenticated, and the user device is validated, decrypt the set of file names to create a set of file names and display the set of file names via the display, and (iii) receive a selection from the user identifying one or more of the set of file names.

Example 8

The system of Example 7, wherein the user device is further configured to: (i) decrypt a set of files from the set of encrypted medical procedure data based upon the selection to create a set of decrypted files and display the set of decrypted files via the display, and (ii) when the set of decrypted files are no longer being displayed via the display, delete the set of decrypted files.

Example 9

The system of Example 7 through 8, wherein the user device is further configured to: (i) decrypt a set of files from the set of encrypted procedure data based upon the selection to create a set of decrypted files and transmit the set of decrypted files to a secure destination associated with the user, and (ii) after transmitting the set of decrypted files, delete the set of decrypted files.

Example 10

The system of any one or more of Examples 1 through 9, wherein the wireless communication device is selected from the group consisting of a Wi-Fi transceiver, a Bluetooth transceiver, and a cellular data transceiver, wherein the data interface is selected from the group consisting of a USB connection and an ethernet connection, and wherein the transfer module is a single board computer.

Example 11

The system of any one or more of Examples 1 through 10, wherein the transfer module is further configured to: (i) receive a configuration data set, the configuration data set comprising a previous key, a new key, and a new key version, (ii) confirm that the current key is different from the new key, (iii) decrypt the set of encrypted procedure data using the previous key to create a second set of medical procedure data, and delete the set of encrypted medical procedure data, (iv) encrypt the second set of medical procedure data using the new key to create a second set of encrypted medical procedure data, and delete the second set of medical procedure data, and (v) update a local configuration to make the device key version equal to the new key version and make the current key equal to the new key.

Example 12

The system of any one or more of Examples 1 through 11, wherein the transfer server is configured to: (i) store a set of email templates, wherein each email template is associated with a user, and wherein each email template is configured to format the set of medical procedure data for transmission to that user, (ii) receive a template request from the user device, wherein the template request comprises an identifier for the user and a terms acceptance, (iii) provide an email template of the set of email templates that is associated with the user to the user device, and (iv) store the terms acceptance, wherein the user terms acceptance describes a legal agreement and an indicator of the user's acceptance of that legal agreement.

Example 13

The system of any one or more of Examples 1 through 12, wherein the transfer module is configured to: (i) provide a web server that the user device may communicate with over the wireless network, and (ii) connect to the wireless network using a static address, wherein the wireless network consists of peers that are either transfer modules such as the transfer module or user devices such as the user device.

Example 14

The system of Example 13, wherein the transfer module is further configured to: (i) restrict the function of the web server to prevent use of a set of commands, the set of commands comprising POST, PUT, and DELETE, (ii) generate a self-signed secure sockets layer certificate, wherein the self-signed secure sockets layer certificate has a duration of time, and (iii) generate a new self-signed secure sockets layer certificate when the duration of time has passed.

Example 15

A method for transferring data from an image guided surgery navigation system comprising the steps: (a) installing a transfer module on the image guided surgery navigation system, the transfer module comprising a storage device, a wireless communication device, and a data interface, wherein the data interface is configured to couple with and receive data from an image guided surgery navigation system, wherein the wireless communication device is configured to connect to a wireless network; (b) receiving a set of medical procedure data from the image guided surgery navigation system at the transfer module; (c) encrypting the set of medical procedure data as a set of encrypted medical procedure data using a current key, storing the encrypted medical procedure data on the storage device, and deleting the set of medical procedure data; and (d) providing the set of encrypted medical procedure data to a user device, the user device comprising a display and a user interface, wherein the user device is in communication with the transfer module over the wireless network.

Example 16

The method of Example 15, further comprising the steps: (a) storing a device key and a device key version, (b) authenticating a user of the user device; (c) validating the user device based upon the device key and the current key; (d) when the user device is not validated, prompting the user for a new key and setting it as the device key, then deleting any information on the user device associated with a previous device key; and (e) when the user device is validated, receiving the set of encrypted procedure data and decrypting the set of encrypted medical procedure data.

Example 17

The method of Example 16, further comprising the steps: (a) receiving a set of authentication data from the user; (b) providing the authentication data to a transfer server; (c) authenticating the user based upon an authentication response from the transfer server; (d) storing a local validation database on the user device, the local validation database comprising a unique hardware identifier, a file description, an encrypted file description, and a key version, wherein the file description and the encrypted file description both describe the same file, and wherein the encrypted file description is created from the file description using the device key; (e) receiving a module identifier and a module key version from the transfer module; and (f) validating the user device when the local validation database contains a record whose key version matches the module key version and whose module identifier matches the unique hardware identifier.

Example 18

The method of any one or more of Examples 15 through 17, further comprising the steps: (a) receiving a configuration data set at the transfer module, the configuration data set comprising a previous key, a new key, and a new key version; (b) confirming that the current key is different from the new key; (c) decrypting the set of encrypted medical procedure data using the previous key to create a second set of medical procedure data, and deleting the set of encrypted medical procedure data; (d) encrypting the second set of medical procedure data using the new key to create a second set of encrypted medical procedure data, and deleting the second set of medical procedure data; and (e) updating a local configuration of the transfer module to make the device key version equal to the new key version and make the current key equal to the new key.

Example 19

The method of any one or more of Examples 15 through 18, further comprising the steps: (a) providing a web server on the transfer module that the user device may communicate with over the wireless network; (b) connecting the transfer module to the wireless network using a static address; (c) restricting the function of the web server to prevent use of a set of commands, the set of commands comprising POST, PUT, and DELETE; (d) generating a self-signed secure sockets layer certificate, wherein the self-signed secure sockets layer certificate has a duration of time; and (e) generating a new self-signed secure sockets layer certificate when the duration of time has passed.

Example 20

A data transfer system comprising: (a) a transfer module comprising a storage device, a wireless communication device, and a data interface, wherein the data interface is configured to couple with and receive data from an image guided surgery navigation system, wherein the wireless communication device is configured to connect to a wireless network via a Wi-Fi or cellular signal; (b) a cloud storage system, wherein the cloud storage system is in communication with the transfer module over the wireless network via a Wi-Fi or cellular signal; and (c) a user device comprising a display and a user interface; wherein the transfer module is configured to: (i) receive a set of medical procedure data from the image guided surgery navigation system, (ii) encrypt the set of medical procedure data as a set of encrypted medical procedure data using a current key, store the encrypted medical procedure data on the storage device, and delete the set of medical procedure data, and (iii) provide the set of encrypted medical procedure data to the cloud storage system; wherein the cloud storage system is configured to: (i) receive a medical procedure data request from the user device, and (ii) provide the set of encrypted medical procedure data to the user device; and wherein the user device is configured to: (i) receive the encrypted medical procedure data from the cloud storage system, (ii) decrypt the medical procedure data, and (ii) display at least some of the medical procedure data to an end user.

Example 21

A data transfer system comprising: (a) a transfer module comprising a storage device, a wireless communication device, and a data interface, wherein the data interface is configured to couple with and receive data from an image guided surgery navigation system, wherein and the wireless communication device is configured to connect to a wireless network; and (b) a user device comprising a display and a user interface, wherein the user device is in communication with the transfer module over the wireless network; wherein the transfer module is configured to: (i) receive a set of medical procedure data from the image guided surgery navigation system, (ii) encrypt the set of medical procedure data as a set of encrypted medical procedure data using a current key, store the encrypted medical procedure data on the storage device, and delete the set of medical procedure data, (iii) receive a medical procedure data request from the user device, and (iv) provide the set of encrypted medical procedure data to the user device; and wherein the user device is configured to: (i) store a local validation database comprising a unique hardware identifier, a file description, an encrypted file description, and a key version, wherein the file description and the encrypted file description both describe the same file, and wherein the encrypted file description is created from the file description using the current key, (ii) receive a module identifier, a module key version, and a file portion associated with the encrypted file description from the transfer module, (iii) decrypt the file portion using the current key to create a decrypted file portion, and validate the user device when: (A) the local validation database contains a record whose key version matches the module key version and whose module identifier matches the unique hardware identifier, (B) the module key version matches the current key version, and (C) the decrypted file portion matches the file description, (iv) when the user device is not validated, prompt the user for a new key and set it as the current key, then delete any information on the user device associated with a previous device key, and (v) when the user device is validated, receive the set of encrypted medical procedure data and decrypt the set of encrypted medical procedure data using the current key.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A data transfer system comprising:
   (a) a transfer module comprising a storage device, a wireless communication device, and a data interface, wherein the data interface is configured to couple with and receive data from an image guided surgery navigation system, wherein the wireless communication device is configured to connect to a wireless network;
   (b) a transfer server configured to provide security and authentication services associated with access to the transfer module; and
   (c) a user device comprising a display and a user interface, wherein the user device is in communication with the transfer module over the wireless network;
   wherein the transfer module is configured to:
      (i) receive a set of medical procedure data from the image guided surgery navigation system,
      (ii) encrypt the set of medical procedure data as a set of encrypted medical procedure data using a current key, store the encrypted medical procedure data on the storage device, and delete the set of medical procedure data,
      (iii) receive a medical procedure data request from the user device, and
      (v) provide the set of encrypted medical procedure data to the user device; and
   wherein the user device is configured to:
      (i) store a device key and a device key version,
      (ii) authenticate a user of the user device,
      (iii) validate the user device based upon the device key and the current key,
      (iv) when the user device is not validated, prompt the user for a new key and set it as the device key, then delete any information on the user device associated with a previous device key; and
      (v) when the user device is validated, receive the set of encrypted procedure data and decrypt the set of encrypted procedure data using the device key.

2. The data transfer system of claim 1, wherein the user device is further configured to:
   (i) receive a set of authentication data from the user,
   (ii) provide the authentication data to the transfer server, and
   (iii) authenticate the user based upon an authentication response from the transfer server.

3. The data transfer system of claim 1, wherein the user device is further configured to:
   (i) store a local validation database comprising a unique hardware identifier, a file description, an encrypted file description, and a key version, wherein the file description and the encrypted file description both describe the same file, and wherein the encrypted file description is created from the file description using the device key,
   (ii) receive a module identifier and a module key version from the transfer module, and
   (iii) validate the user device when the local validation database contains a record whose key version matches the module key version and whose module identifier matches the unique hardware identifier.

4. The data transfer system of claim 1, wherein the user device is further configured to:
   (i) receive a module key version from the transfer module, and
   (ii) validate the user device when the module key version matches the device key version.

5. The data transfer system of 1, wherein the user device is further configured to:
(i) store a local validation database comprising a file description and an encrypted file description, wherein the file description and the encrypted file description both describe a file stored on the transfer module, and wherein the encrypted file description is created from the file description using the device key,
(ii) request a file portion associated with the encrypted file description from the transfer module,
(iii) decrypt the file portion using the device key to create a decrypted file portion, and
(iv) validate the user device where the decrypted file portion matches the file description.

6. The data transfer system of claim 1, wherein the user device is further configured to:
(i) select a set of encrypted file names from the set of encrypted medical procedure data,
(ii) where the user is authenticated, and the user device is validated, decrypt the set of file names to create a set of file names and display the set of file names via the display, and
(iii) receive a selection from the user identifying one or more of the set of file names.

7. The data transfer system of claim 6, wherein the user device is further configured to:
(i) decrypt a set of files from the set of encrypted medical procedure data based upon the selection to create a set of decrypted files and display the set of decrypted files via the display, and
(ii) when the set of decrypted files are no longer being displayed via the display, delete the set of decrypted files.

8. The data transfer system of claim 6, wherein the user device is further configured to:
(i) decrypt a set of files from the set of encrypted procedure data based upon the selection to create a set of decrypted files and transmit the set of decrypted files to a secure destination associated with the user, and
(ii) after transmitting the set of decrypted files, delete the set of decrypted files.

9. The data transfer system of claim 1, wherein the wireless communication device is selected from the group consisting of a Wi-Fi transceiver, a Bluetooth transceiver, and a cellular data transceiver, wherein the data interface is selected from the group consisting of a USB connection and an ethernet connection, and wherein the transfer module is a single board computer.

10. The data transfer system of claim 1, wherein the transfer module is further configured to:
(i) receive a configuration data set, the configuration data set comprising a previous key, a new key, and a new key version,
(ii) confirm that the current key is different from the new key,
(iii) decrypt the set of encrypted procedure data using the previous key to create a second set of medical procedure data, and delete the set of encrypted medical procedure data,
(iv) encrypt the second set of medical procedure data using the new key to create a second set of encrypted medical procedure data, and delete the second set of medical procedure data, and
(v) update a local configuration to make the device key version equal to the new key version and make the current key equal to the new key.

11. The data transfer system of claim 1, wherein the transfer server is configured to:
(i) store a set of email templates, wherein each email template is associated with a user, and wherein each email template is configured to format the set of medical procedure data for transmission to that user,
(ii) receive a template request from the user device, wherein the template request comprises an identifier for the user and a terms acceptance,
(iii) provide an email template of the set of email templates that is associated with the user to the user device, and
(iv) store the terms acceptance,
wherein the user terms acceptance describes a legal agreement and an indicator of the user's acceptance of that legal agreement.

12. The data transfer system of claim 1, wherein the transfer module is configured to:
(i) provide a web server that the user device may communicate with over the wireless network, and
(ii) connect to the wireless network using a static address,
wherein the wireless network consists of peers that are either transfer modules such as the transfer module or user devices such as the user device.

13. The data transfer system of claim 12, wherein the transfer module is further configured to:
(i) restrict the function of the web server to prevent use of a set of commands, the set of commands comprising POST, PUT, and DELETE,
(ii) generate a self-signed secure sockets layer certificate, wherein the self-signed secure sockets layer certificate has a duration of time, and
(iii) generate a new self-signed secure sockets layer certificate when the duration of time has passed.

14. The data transfer system of claim 1, wherein the transfer module is further configured to:
(i) transmit a validation request to a third-party device, and
(ii) receive a validation approval from the validation request.

15. A method for transferring data from an image guided surgery navigation system comprising the steps:
(a) installing a transfer module on the image guided surgery navigation system, the transfer module comprising a storage device, a wireless communication device, and a data interface, wherein the data interface is configured to couple with and receive data from an image guided surgery navigation system, wherein the wireless communication device is configured to connect to a wireless network;
(b) receiving a set of medical procedure data from the image guided surgery navigation system at the transfer module;
(c) encrypting the set of medical procedure data as a set of encrypted medical procedure data using a current key, storing the encrypted medical procedure data on the storage device, and deleting the set of medical procedure data;
(d) storing a device key and a device key version;
(e) authenticating a user of a user device;
(f) validating the user device based upon the device key and the current key;
(g) when the user device is not validated, prompting the user for a new key and setting it as the device key, then deleting any information on the user device associated with a previous device key; and (h) when the user device is validated, receiving the set of encrypted medical procedure data and decrypting the set of encrypted procedure data.

16. The method of claim 15, further comprising the steps:
(a) receiving a set of authentication data from the user;
(b) providing the authentication data to a transfer server;
(c) authenticating the user based upon an authentication response from the transfer server;
(d) storing a local validation database on the user device, the local validation database comprising a unique hardware identifier, a file description, an encrypted file description, and a key version, wherein the file description and the encrypted file description both describe the same file, and wherein the encrypted file description is created from the file description using the device key;
(e) receiving a module identifier and a module key version from the transfer module; and
(f) validating the user device when the local validation database contains a record whose key version matches the module key version and whose module identifier matches the unique hardware identifier.

17. The method of claim 15, further comprising the steps:
(a) receiving a configuration data set at the transfer module, the configuration data set comprising a previous key, a new key, and a new key version;
(b) confirming that the current key is different from the new key;
(c) decrypting the set of encrypted medical procedure data using the previous key to create a second set of medical procedure data, and deleting the set of encrypted medical procedure data;
(d) encrypting the second set of medical procedure data using the new key to create a second set of encrypted medical procedure data, and deleting the second set of medical procedure data; and
(e) updating a local configuration of the transfer module to make the device key version equal to the new key version and make the current key equal to the new key.

18. The method of claim 15, further comprising the steps:
(a) providing a web server on the transfer module that the user device may communicate with over the wireless network;
(b) connecting the transfer module to the wireless network using a static address;
(c) restricting the function of the web server to prevent use of a set of commands, the set of commands comprising POST, PUT, and DELETE;
(d) generating a self-signed secure sockets layer certificate, wherein the self-signed secure sockets layer certificate has a duration of time; and
(e) generating a new self-signed secure sockets layer certificate when the duration of time has passed.

19. The method of claim 15, further including:
providing the set of encrypted medical procedure data to the user device, the user device comprising a display and a user interface, wherein the user device is in communication with the transfer module over the wireless network.

* * * * *